United States Patent [19]
Lee

[11] Patent Number: 5,891,084
[45] Date of Patent: Apr. 6, 1999

[54] MULTIPLE CHAMBER CATHETER DELIVERY SYSTEM

[76] Inventor: Vincent W. Lee, 10 Bull Run, Irvine, Calif. 92720

[21] Appl. No.: 789,501

[22] Filed: Jan. 27, 1997

Related U.S. Application Data

[63] Continuation of Ser. No. 364,859, Dec. 27, 1994, abandoned.

[51] Int. Cl.⁶ .................................................. A61M 31/00
[52] U.S. Cl. ............................................... 604/54; 604/96
[58] Field of Search ................................. 604/49, 54, 96, 604/164, 171, 173, 174, 264, 280, 289, 290, 294

[56] References Cited

U.S. PATENT DOCUMENTS

| | | | |
|---|---|---|---|
| 3,593,713 | 7/1971 | Bogoff | 604/27 X |
| 3,788,328 | 1/1974 | Alley et al. | |
| 4,299,227 | 11/1981 | Lincoff | |
| 4,327,734 | 5/1982 | White | |
| 4,645,504 | 2/1987 | Byers | 623/1 |
| 5,092,837 | 3/1992 | Ritch et al. | 604/8 |
| 5,282,785 | 2/1994 | Shapland et al. | |
| 5,286,254 | 2/1994 | Shapland et al. | |
| 5,295,962 | 3/1994 | Crocker et al. | |
| 5,304,118 | 4/1994 | Trese et al. | 604/51 |
| 5,342,297 | 8/1994 | Jang | 604/53 |
| 5,370,607 | 12/1994 | Memmen | 604/8 |
| 5,372,584 | 12/1994 | Zink et al. | 604/55 |
| 5,558,652 | 9/1996 | Henke | 604/280 |

*Primary Examiner*—Corrine M. McDermott
*Attorney, Agent, or Firm*—Maria Erlinda C. Sarno

[57] ABSTRACT

A catheter system comprising of a catheter sheath and a multichamber balloon catheter capable of simultaneous or sequential delivery of substances such as drugs, anesthetics, biologicals or wound modulating agents into an organ or tissue remote from the point of entry of the catheter system. A specific use of such catheter system is for the timed application of wound modulating agents prior to the formation of a fistula in the filtration procedure used for the management of glaucoma. Another use is for the application and subsequent washing of the scar formation with wound modulating agents after an unsuccessful glaucoma filtration procedure. Substances requiring controlled release is applied through one lumen of the balloon catheter whose exit port is covered with a semipermeable or microporous membrane. Other substances not requiring controlled or slow release is applied through a second lumen where the substance can exit freely through a hole at one end of the second lumen. Retrieval of applied substances is also possible through gentle suction from the second lumen or a third lumen if needed.

12 Claims, 7 Drawing Sheets

MULTIPLE CHAMBER CATHETER DELIVERY SYSTEM

This is a continuation of application Ser. No. 08/364,859 filed Dec. 27, 1994 which was abandoned upon filing hereof.

BACKGROUND

The present invention relates to a catheter system having several components that is capable of delivering a drug, medication or any desirable substance into a selected site. These substances are usually applied to the desired site prior to making an incision or surgery on the same site. The present delivery systems usually involve a single catheter with an inflatable balloon made up of either a permeable or semipermeable material. Examples of the balloon catheters used for different applications are illustrated in U.S. Pat. No. 5,286,254 issued to Shapland et al., U.S. Pat. No. 4,299,227 issued to Harvey A. Lincoff, U.S. Pat. No. 4,327,734 issued to Robert I. White, Jr., U.S. Pat. No. 3,788,328 issued to Ralph D. Alley and David S. Sheridan and U.S. Pat. No. 5,100,383 issued to Meir Lichtenstein. The present invention is constructed differently from the other balloon catheters and the delivery system is composed of several parts. One specific application of this invention relates to the use of the catheter system in the management of glaucoma.

There are many techniques for delivering drugs and other substances or medication to body tissues and organs. These include among possible others, oral administration, injection directly into body tissue, topical administration, transcutaneous administration and intravenous administration. Direct injection into the tissue, oral administration, or intravenous administration typically delivers the desired substance into the blood stream and therefore tend to be systemic. Topical and transcutaneous administration tend to deliver the drug, medication or desired substance into a localized area. The drug, medication or desired substance is usually absorbed into or across the skin or tissue. Topical and transcutaneous application are suitable delivery systems if the desired site of application is the skin or tissues proximate to the skin and passive absorption of the drug or substance by the surrounding tissue is not critical. Although many medical situation are satisfactorily treated or managed by these various techniques, there is a need for a system that can deliver a drug or other desired substance into a localized area of an internal tissue or organ without appreciably affecting the surrounding tissues. This system would be particularly useful when an incision is subsequently made on the site after the localized application of the drug or substance.

There are several applications for which such system would be desirable. This system can be used to apply substances, medication or drugs such as antibiotics, anesthetics, and wound modulating agents like antimetabolites to a tissue or organ remote to the external parts of the body prior to an incision or surgery at the site of application. One particular application is the application of wound modulating agents to the episcleral space of the eye prior to the fistulizing step in the glaucoma filtering procedure. The filtering procedure is employed to manage glaucoma. Another particular application is for delivering wound modulating agents such as antimetabolites to scars subsequently formed after an unsuccessful glaucoma filtering procedure to enable formation of more permanent escape channels for the aqueous humor. Still another particular application is for delivering wound modulating agents to scars formed on and around implants placed in the fistula during the filtering procedure. The implants are placed to keep the fistula open. The implants consist of a wide variety of foreign materials placed in the fistula such as stripe of hydrogel with parallel capillary channels, tubes and valves made of biocompatible materials.

Glaucoma is a leading cause of irreversible blindness throughout the world. Glaucoma is characterized by widely diverse clinical and histopathologic manifestation. However, all glaucomas can be generalized as situations in which the intraocular pressure (hereinafter referred to as IOP) is too high for the normal functioning of the optic nerve head. Damage to the optic nerve head is associated with progressive loss and constriction of the visual field, and it is this which, if untreated, can lead to total, irreversible blindness. Blindness from glaucoma is preventable but requires early detection and proper treatment. Once the blindness of glaucoma has occurred, there is no known treatment that will restore the lost vision. Detection depends on the ability to recognize the early clinical manifestations of the various glaucomas, while appropriate treatment requires an understanding of the pathogenic mechanism involved, as well as a detailed knowledge of the drugs and surgical procedures that are used to control the IOP. In the eye, the bulk of aqueous humor which is produced by the ciliary processes flows through the pupil into the anterior chamber and leaves the eye via structures in the anterior chamber angle, primarily through the trabecular meshwork and Schlemm's canal with a small contribution from anterior uveal absorption. From Schlemm's canal, the aqueous humor passes through intrascleral channels to reunite with the blood stream in the episcleral veins. The normal pressure in these vessels is 8 to 11 mm Hg which contribute directly to the IOP. A rise in IOP occurs when the rate at which aqueous humor enters the eye is greater than the rate at which it leaves the eye.

One means for lowering the IOP in glaucoma patients is through the glaucoma filtering procedure. This procedure generally involves providing a limbal fistula through which the aqueous humor can drain into a subconjunctival space and subsequently filter into the conjunctiva. A limbal fistula means an opening at the limbus of the eye. There are two basic types of fistulas, a full thickness and a partial thickness fistula. A full thickness fistula is a direct opening through the full thickness of the limbal tissue. A partial thickness fistula is a fistula having a partial thickness scleral flap over it. There are several means for creating the fistula and there are also several variations for performing the filtering procedure. The present means usually involves formation of a scleral flap prior to the formation of the fistula. A scleral flap is usually formed by making a limbus-based conjunctival flap followed by dissection of a desired area of the sclera. Shields, M. B. (1982) *Textbook of Glaucoma*, 1st ed. pages 461–497 describes the different fistulizing techniques and filtering procedure. Most successful glaucoma filtering procedure are characterized by a fistula that remains open for the free flow of the aqueous humor. The most common cause of failure in glaucoma filtering surgery is scarring at the fistula and the immediate area around the filtering site. This usually occurs external to the scleral flap at the level of the conjunctiva-Tenon's capsule-episcleral interface. Scarring is characterized by an increased amount of collagen produced by the proliferation of fibroblasts which eventually blocks the fistula thereby preventing the free flow of the aqueous humor and the patient reverts back to the glaucoma condition. Preoperative and postoperative inflammation frequently also contributes to the scarring. A larger incision made prior to the formation of the fistula is expected to cause more inflammation thereby aggravating the scarring situation. Antimetabolites such as 5-fluorouracil, cytosine arabinoside, bleomycin, and doxorubicin had been shown to inhibit fibroblast proliferation. The antimetabolite treatment increases the success rate of the filtering procedure. Presently, the antimetabolite such as 5-fluorouracil (hereinafter referred to as fluorouracil) is usually injected subconjunctivally, several degrees from the operative site, several times after the glaucoma filtering procedure. Alternatively, fluorouracil is also given intraoperatively followed by the postoperative subconjunctival injections. Dose and frequency of injection differ according to the type of glaucoma. These treatment regimens are well documented in the literature. The necessity of multiple subconjunctival injections which inconvenience the patient coupled with the high incidence of conjunctival and corneal epithelial toxic effects manifested by conjunctival wound leaks and corneal epithelial defects have limited the widespread application of fluorouracil. Conjunctival wound leaks usually results from the passing of the aqueous humor from the filtering site directly through the conjunctival needle tracts because fluorouracil also effectively inhibits the conjunctival wound healing of the needle tracts which are formed during the suturing of the scleral flap after the filtering procedure. Wound modulating agents such as the antimetabolite fluorouracil inhibit fibroblast proliferation which affect collagen formation, resulting into inhibition of wound healing. Other wound modulating agents such as alkylating drugs or agents and natural alkaloids may also inhibit fibroblast proliferation. Examples of these wound modulating agents are mechlorethamine, cyclophosphamide, chlorambucil, melphalan, aziridine, alkyl sulfonate, carmustine, lomustine, semustine, triazene, streptozocin, methotrexate, cytarabine, mercaptopurine, thioguanine, vinblastine, vincristine, dactinomycin, daunorubicin, doxorubicin HCl, bleomycin, mitomycin, and plicamycin. Further caution is required on the use of wound modulating agents, in general, due to the reported complications of unexpectedn hypotony observed with its use. Hypotony means an intraocular pressure lower than 5 mm Hg.

Mitomycin-C, an example of a wound modulating agent, is an alkylating agent isolated from *Streptomyces caespitosus*, which can be used as an alternative to fluorouracil. Because Mitomycin-C (hereinafter referred to as mitomycin) can penetrate the anterior chamber and also cause endothelial damage, mitomycin unlike fluorcuracil, cannot be injected subconjunctivally after the filtering procedure. However, a single intraoperative application of mitomycin at the filtering site has been shown to be sufficient in inhibiting fibroblast proliferation because it is at least one hundred times more potent than fluorouracil. See Ando, Ido, Kawai, Yamamoto and Kitazawa, Inhibition of Corneal Epithelial Wound Healing, Ophthalmology 99:1809, Kitazawa, Kawase, Matsushita and Minobe, *Trabeculectomy With Mitomycin*, Arch. Ophthalmol. 109:1693, and Zacharia, Deppermann and Schuman, Ocular Hypotony After Trabeculectomy With Mitomycin C, Amer. J. Ophthalmol. 116:314. Intraoperative application of fluorouracil as used in the mitomycin treatment, even at higher concentrations and longer exposure times do not produce the same results as mitomycin. Mitomycin treatment, therefore, has greater success rates in the management of glaucoma compared to fluorouracil especially in patients with complicated glaucomas such as neovascular glaucoma, inflammatory glaucoma and patients whose previous filtration procedure had failed. This feature compared to multiple subconjunctival injection and the reduced incidence of corneal toxic effect brought about by the focal application of mitomycin are the major attractions of the mitomycin treatment. The primary effect of mitomycin appears to be a cytocidal effect on subconjunctival fibroblasts at the filtering site. One disadvantage of using mitomycin is the observed greater incidence of hypotony with mitomycin compared to fluorouracil. Hypotony in mitomycin treatment can generally be prevented by lower concentrations and less exposure times. The recommended time for mitomycin application is less than five minutes. Therefore, a process that results in a focal and timed exposure of mitomycin to the tissue is needed in order to limit its toxic effects. An application system capable of delivering a more concentrated mitomycin at a limited area for a controlled period of time is required as a delivery tool for the development of an application process that will result in a successful filtering procedure for the management of glaucoma.

Several techniques for the intraoperative application of mitomycin in filtering procedures are described in published literature. See Kitazawa, Kawase, Matsushita and Minobe, Trabeculectomy with Mitomycin, Arch. Ophthalmol. 109:1693–1698, Skuta, Beeson, Higginbotham, Lichter, Musch, Bergstrom, Klein, and Falck, Intraoperative Mitomycin versus Postoperative 5-Fluorouracil in High-risk Glaucoma Filtering Surgery, Ophthalmology 99:438–444, Palmer, Mitomycin as Adjunct Chemotherapy with Trabeculectomy, Ophthalmology 98:317–321, Kitazawa, Matsushita, Yamamoto, and Kawase, Low-dose and High-dose Mitomycin Trabeculectomy as an Initial Surgery in Primary Open-angle Glaucoma, Ophthalmology 100:1624–1628, Shields, Scroggs, Sloop and Simmons, Clinical and Histopathologic Observations Concerning Hypotony after Trabeculectomy with Adjunctive Mitomycin C, Amer. J. Ophthalmol. 116:673–683, Khaw, Doyle, Sherwood, Grierson, Schultz, and McGorray prolonged Localized Tissue Effects from 5-Minute Exposures to Fluorouracil and Mitomycin C, Arch. Ophthalmol. 111:263–267, and Wise, Mitomycin-Compatible Suture Technique for Fornix-Based Conjunctival Flaps in Glaucoma Filtration Surgery, Arch. Ophthalmol. 111:992–997. Although these procedures may differ slightly, the intraoperative application of mitomycin generally involves soaking a piece of sponge into a mitomycin solution and contacting the soaked sponge to the exposed scleral surface over the planned filtration site for a controlled period of time, generally less than 5 minutes or sequentially at several one minute exposures for a total of 5 minutes of tissue exposure. This is usually followed by a washing procedure to wash off the mitomycin from the filtration site. The present use of sponge for mitomycin application causes exposure of a wider surface of tissue than is required. As mentioned above, although mitomycin application prevents the scarring of the fistula, it is also more potent and more toxic to the exposed tissues than fluorouracil.

One object of the invention is to provide a catheter system capable of a timed introduction of a desired substance with minimal surgical disturbance resulting in less inflammation compared to the current procedure employed in the formation of the scleral flap. Another object of the invention is to provide a catheter system for introducing a desired but generally toxic substance into a localized area for a given length of time where prolonged exposure to the surrounding areas is not desirable. Examples of these substances are wound modulating agents such as antimetabolites alkylating drugs or agents, natural alkaloids and other fibroblast proliferation inhibiting agents which reduce collagen response to injury. Still another object of this invention is to demonstrate a process using the catheter system for introducing a desired but generally toxic substance like mitomycin prior to the fistulizing step of the filtering procedure used in the management of glaucoma. A further object of the invention is to show the use of the catheter system in correcting conditions where the glaucoma filtration procedure failed due to scar formation.

SUMMARY AND DESCRIPTION OF THE INVENTION

The present invention provides a catheter system useful for delivering any desirable substance to a particular site of an internal tissue or organ remote to the external parts of the body with minimal undesirable effects to the surrounding tissue. The term catheter is intended to broadly include any medical device intended for insertion into a body tissue or organ to permit injection of desired substances into a localized area.

A method using the catheter system of the present invention involves making an initial incision for introduction of a catheter sheath; anchoring the catheter sheath in place, if desired; and, applying a desired substance through a balloon catheter inserted into the catheter sheath. A washing solution or another solution may be introduced from a separate chamber of the same balloon catheter, if desired.

A specific application of the method aspect of using the catheter system in the filtration procedure for managing glaucoma is illustrated first followed by a discussion on how the same catheter system can be used for scar revision to repair previous filtration procedures which have failed.

Figure 1:
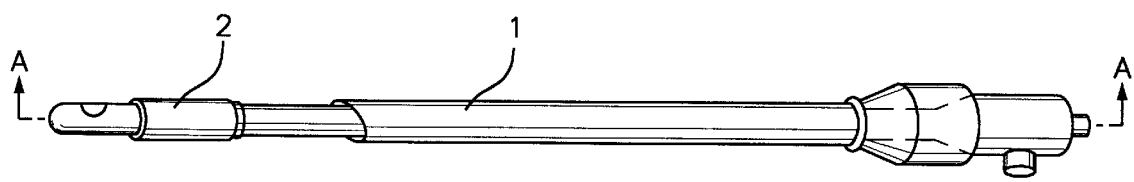
FIG. 1 illustrate the main components of the catheter system, the catheter sheath and the balloon catheter.
Figure 2:
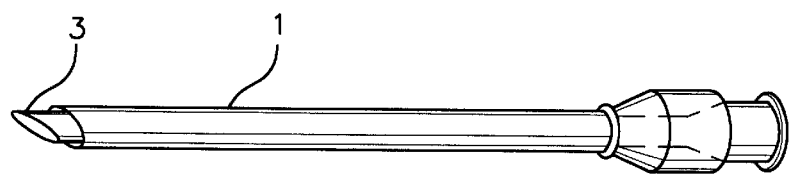
FIG. 2 illustrates a needle inside the catheter sheath.
Figure 3A:
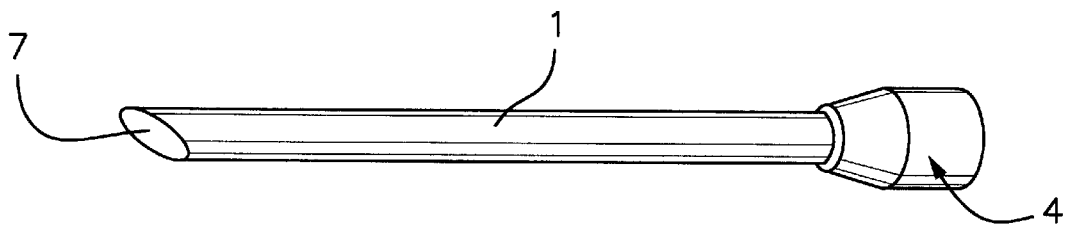
FIG. 3A illustrates a straight tubular catheter sheath.
Figure 3B:
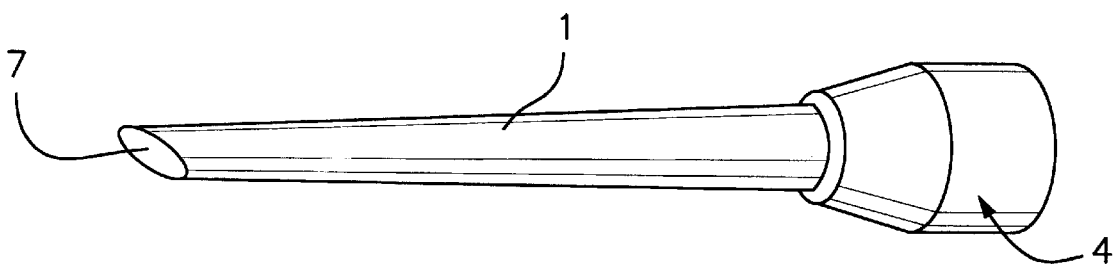
FIG. 3B illustrates a tapered catheter sheath.
Figure 4:
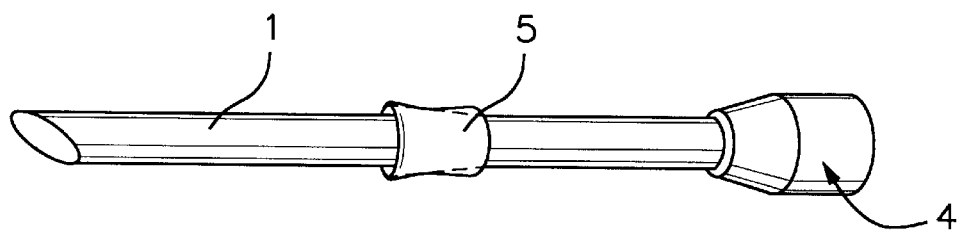
FIG. 4 illustrates a catheter sheath with a sleeve a slightly tapered horizontal bore within the sleeve.
Figure 4A:
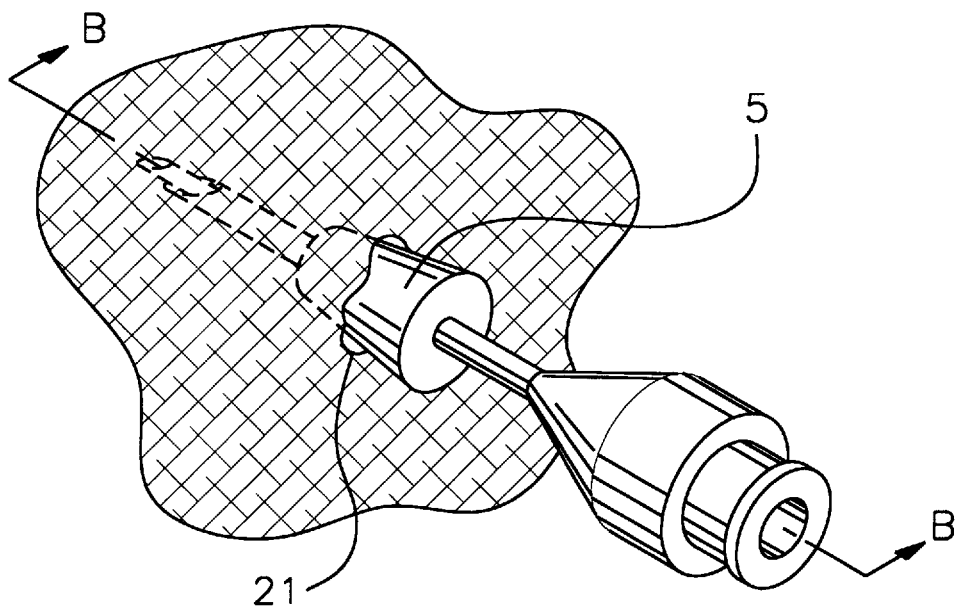
FIG. 4A illustrates a sleeve anchoring the catheter sheath to tissues by tamponing mechanism.
Figure 4B:
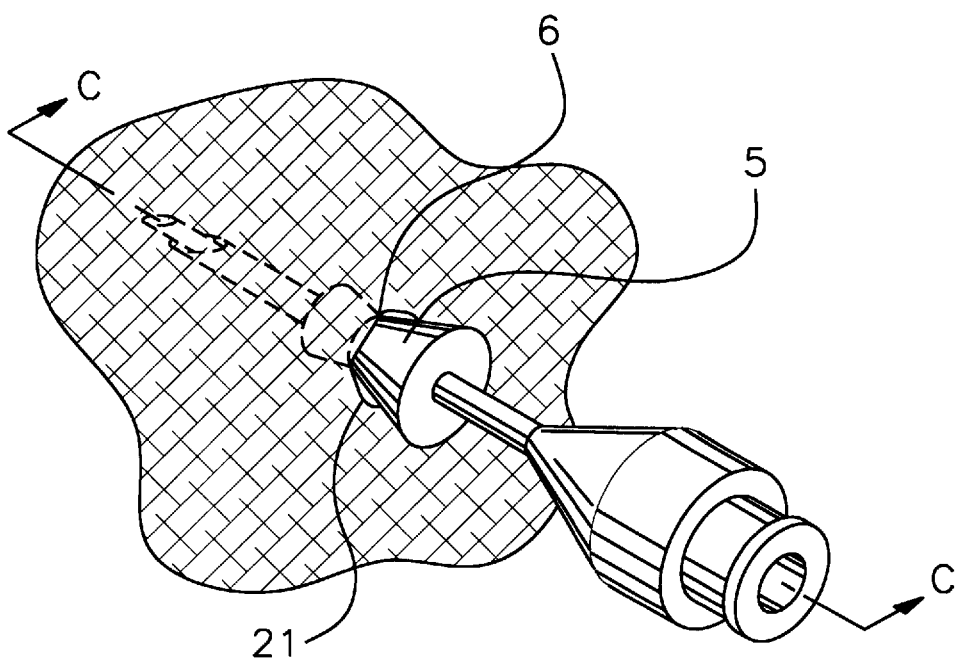
FIG. 4B illustrates a sleeve anchoring the catheter sheath to tissues by advancing the tissue into its recessed plane.
Figure 5A:
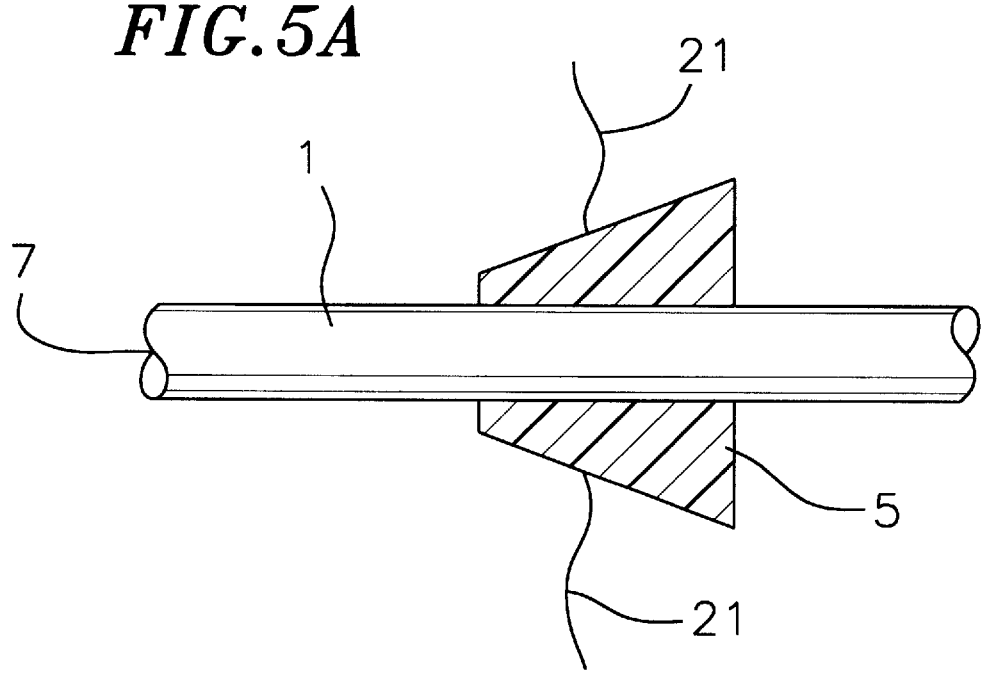
FIG. 5A is a cross-sectional view of the sleeve taken on the line B—B of FIG. 4A.
Figure 5B:
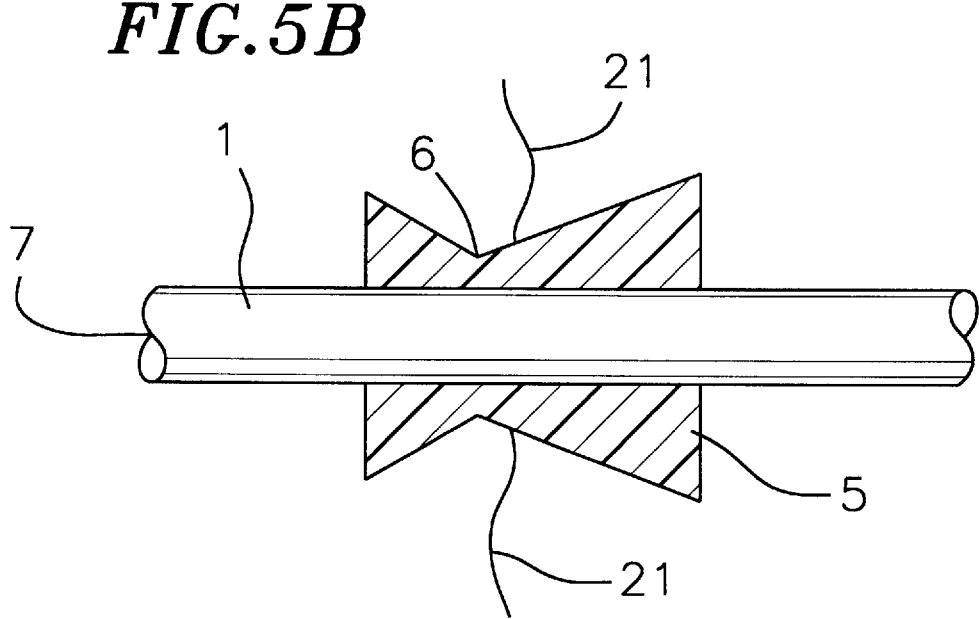
FIG. 5B is a cross-sectional view of the sleeve taken on the line C—C FIG. 4B.
Figure 6:
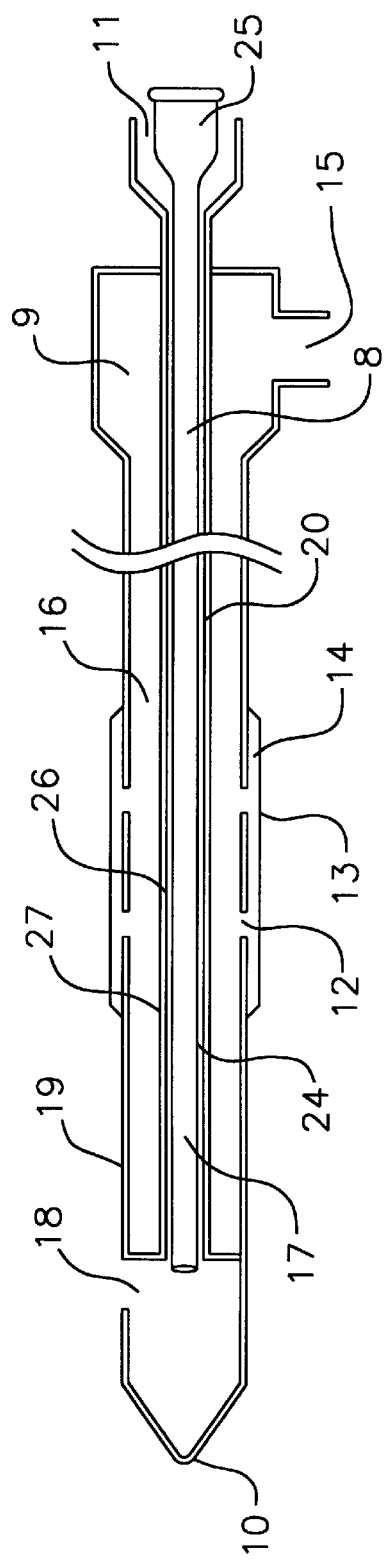
FIG. 6 is a cross-sectional view of the balloon catheter in a deflated state taken on the line A—A of FIG. 1 showing the point of introduction of a cannula.
Figure 7:
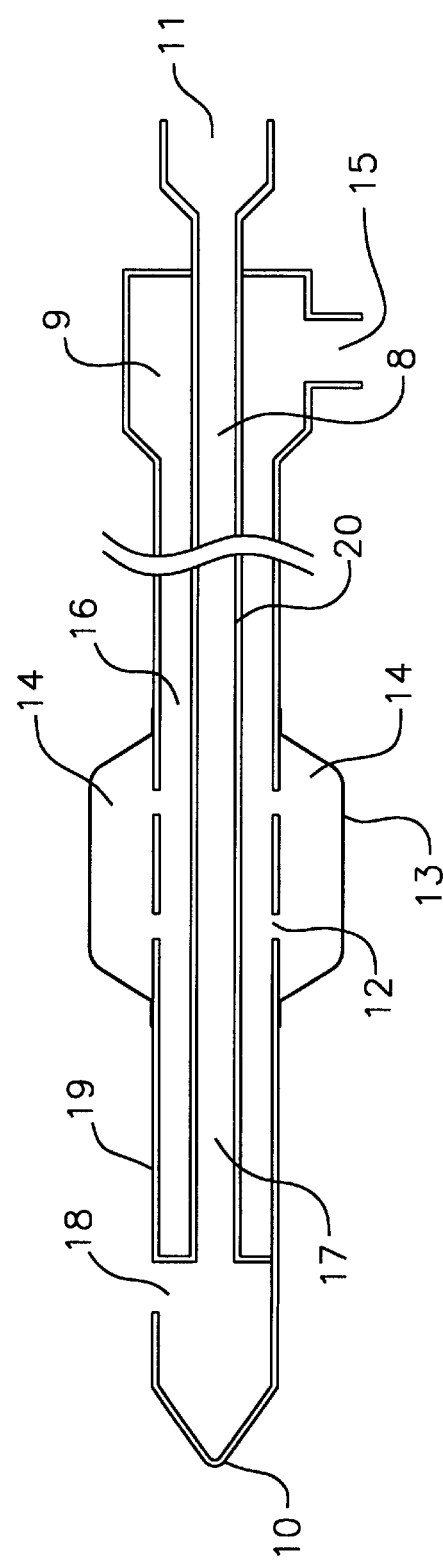
FIG. 7 is a cross-sectional view of the balloon catheter in an inflated state taken on the line A—A of FIG. 1.
Figure 8A:
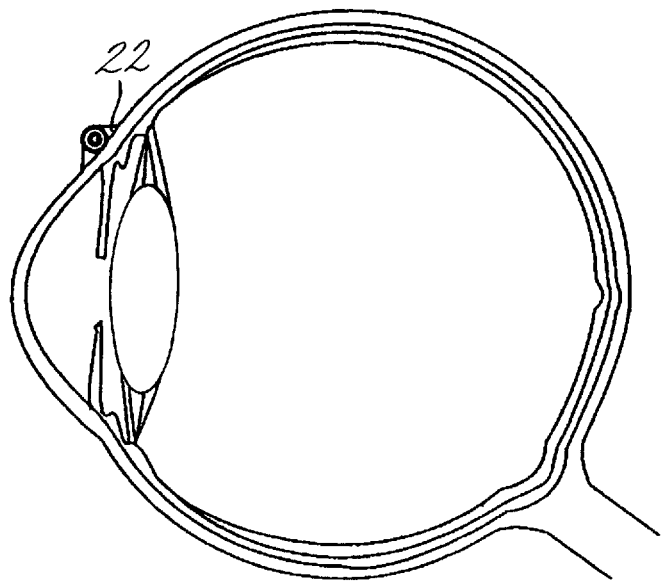
FIG. 8A is a sagittal section of the eye showing the balloon catheter at the episcleral space of the eye.
Figure 8B:
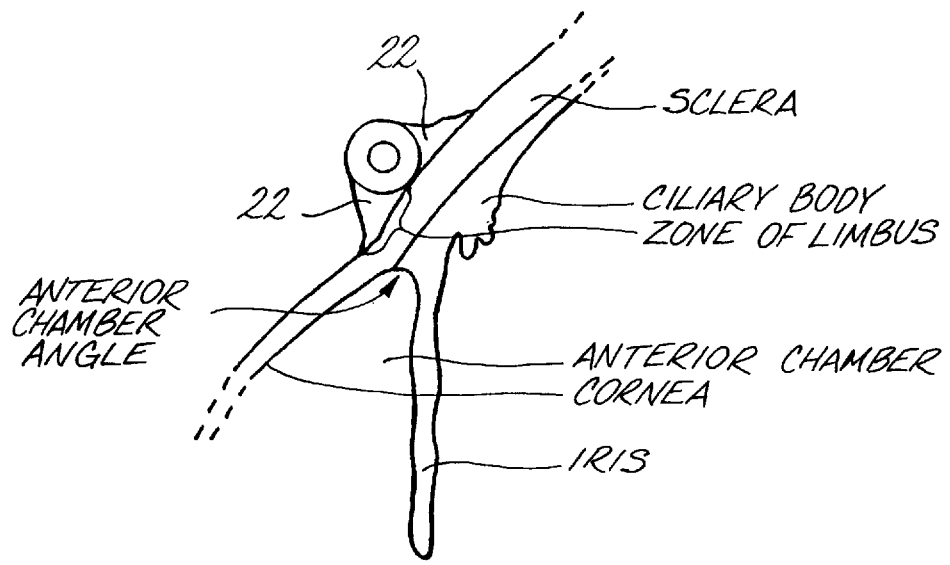
FIG. 8B is an enlarged view showing the cross section of the catheter on the episcleral space of the eye.

The use of the catheter system whose main components are shown in FIG. 1 for the management of glaucoma involves making an initial incision on the subconjunctiva of the eye by entry of a needle 3 placed within a catheter sheath 1 as shown in FIG. 2. The needle is preferably one with a luer lock end opposite the sharp tip. The catheter sheath has a tubular shaft with one end having an enlarged opening 4 to allow introduction of other devices through the lumen 7 of the catheter sheath as shown in FIGS. 3A and 3B. As used in the glaucoma filtration procedure, at full insertion of the needle 3 inside the catheter sheath, the sharp tip opposite the luer lock end of the needle protrudes at least one millimeter longer than the distal tip of the catheter sheath 1. As used in this invention, the distal end is the point away from the operator while the proximal end is the point close to the operator during the use of the device. Using the needle inserted through the catheter sheath to make an incision ensures that the opening made is of a size just sufficient to allow entry of the catheter sheath covering the needle. The size of the incision made is dependent upon the outer diameter of the catheter sheath used. For the glaucoma procedure, the catheter sheath is preferably 0.75 inch in length and of an inner diameter that will allow entry of a 16 gauge needle. The catheter sheath can vary in length depending upon the distance of the point of insertion from the site of application. The catheter sheath 1 may be straight tubular as shown in FIG. 3A or the catheter sheath may be tapered with one end having a larger diameter than the other end as shown in FIG. 3B. The end having a larger diameter is at the proximal end of the catheter sheath and is connected to the enlarged opening 4 of the catheter sheath as shown in FIG. 3B. The tapered configuration will allow the catheter sheath to anchor at the incision site at the point where the diameter of the catheter sheath is larger than the incision made. In the preferred embodiment, the needle for making an incision is a hypodermic 16 gauge syringe with an enlarged opening at one end such as a luer lock. The needle 3 is retrieved from the catheter sheath after entry of the catheter sheath into the subconjunctival space. The catheter sheath may be advanced further to the desired location of the eye after retrieval of the needle 3. For the glaucoma filtration procedure, the catheter sheath having a hold means is preferably advanced to the episcleral space 22 near the limbus of the eye where the fistula will be formed. When the catheter sheath 1 is at its desired location, an example of a holding means a sleeve 5 may be used to keep the catheter sheath in place. The sleeve is allowed to slide towards the distal end of the catheter sheath 1 until the sleeve 5 communicates with the tissue surrounding the catheter sheath 1. When using a straight tubular catheter sheath 1, the sleeve has a bore diameter slightly larger than the outer diameter of the distal end of the catheter sheath 1. The bore within the sleeve is preferably tapered such that the inner diameter of the proximal end of the sleeve is slightly smaller than the inner diameter of the distal end to position the sleeve at the proximal end of the catheter sheath 1 prior to use as shown in FIG. 4. The slightly tapered bore configuration will prevent the sleeve from sliding down the catheter sheath on its own prior to use. The catheter sheath 1 is anchored to the tissue by sliding the sleeve 5 to the incision site and lodging the sleeve through tamponing as shown in FIG. 4A or by advancing sleeve 5 into the surrounding tissue around the catheter sheath 1 until the tissue surrounding the incision clasp into the recessed portion 6 of the sleeve 5 as shown in FIG. 4B. Figures 5A and 5B show the cross sectional view of the two configurations of the sleeve described along the lines B—B and C—C respectively. Anchoring the catheter sheath 1 at the incision site prevents excessive movement of the devices during the surgical process as well as enable the devices used to target a precise location of the tissue or organ 21. To administer, apply or deliver a desired substance at a controlled rate and at a precise location of the tissue, a balloon catheter 2 with an expandable semipermeable or microporous membrane is inserted through the lumen 7 of the catheter sheath 1 as shown in FIG. 1. The desired substance may be varied depending upon the application to which the desired substance will be used. The balloon catheter 2 has an outer diameter less than the inner diameter of the catheter sheath 1 to allow easy introduction through the lumen 7 of the catheter sheath. When used in the present invention, the balloon catheter is preferably 1.25 inch in length and 0.5 inch longer than the catheter sheath. The distal end of the balloon catheter protruding from the tip of the catheter sheath exposes the entire surface area of the expandable membrane as shown in FIG. 1. Prior to and during insertion of the balloon catheter 2 into the catheter sheath 1, the device is in a collapsed or deflated state as shown in FIG. 6. In the preferred embodiment, the semipermeable or microporous membranes are those effective to permit transport or passage of the drug or wound modulating agents such as mitomycin across the expandable membrane surface as a result of an appropriate driving force. Example of wound healing agents are alkylating drugs or alkylating agents, antimetabolites and natural alkaloids. Appropriate driving force are known in the art which includes pressure, iontophoresis, and phonophoresis. When pressure is employed to drive a drug to a target area, regulation means known to those skilled in the art such as compressor, regulator or syringe pump can be used to apply sufficient pressure to deliver the desired substance to the target area without further traumatization of the internal body tissue. Nonpressure transport force for assisting the delivery of the desired substance to a body tissue in conjunction with the semipermeable or microporous membrane aid in controlling the transfer or flow of the desired substance from the balloon catheter. Use of nonpressure transport force minimize the pressure driven diffusion or outward flow of fluid caused by the slight pressure involved in filling the balloon chamber 14 of the balloon catheter with the agent which is delivered through the opening 15 and into the lumen 16 of chamber 9 within the balloon catheter as shown by FIGS. 6 and 7. It is also contemplated that other transport forces can be used. Instantaneous application that allows rapid spread of the desired substance in a wide area such as the wound modulating agents is not desirable. Delivering the desired substance through a semipermeable or microporous membrane solves this problem. The semipermeable or microporous membrane does not allow instantaneous spread of the substance. A driving force has to be applied to get the substance across the membrane. Therefore, control of this driving force will regulate the flow of the desired substance effectively. An amount just sufficient to wet the surface of the expandable membrane and the surrounding tissues around the expandable membrane is desired to localize the substance contact with the tissue. FIG. 8 shows the sagittal section of the eye and the location of the balloon catheter at the episcleral space 22 of the eye for the agent or drug application.

The preferred wound modulating agent used in the present invention, mitomycin, is toxic to the exposed tissue. An acceptable concentration of the mitomycin for this invention is 0.001–0.06%. The present recommended time of exposure is less than 5 minutes. The present invention does not intend to limit tie time exposure to the present practice but considers that the time of exposure may vary with the change in the method of agent application and the nature of the wound modulating agent used. To enable the effective and nondeleterous application of the wound modulating agent, the agent is immediately withdrawn from the balloon catheter chamber 9 after the desire time of agent contact with the tissue is achieved. The method of withdrawal will be dictated by the means used to introduce the wound modulating agent. In the case when nonpressure force is used, the driving mechanism is likewise terminated after the desired time of wound modulating agent contact with the tissue is achieved. When used in the glaucoma filtration procedure, it is preferred to wash off immediately the applied wound modulating agent from the site of application. The balloon catheter 2 of this invention as shown in FIGS. 6 and 7 allow immediate introduction of the washing solution there are no membranes covering the distal opening 18 and the proximate opening 11 of chamber 8. The washing solution is introduced at opening 11 and delivered through the central lumen 17 of chamber 8 of the balloon catheter. Preferably, as shown in FIG. 6 the central lumen 17 is of a diameter that will allow the introduction of a 20 gauge cannula 24 with an open distal tip and an open proximate end 25 which is connected to a syringe pump or a tubing connected to a delivery pump. The washing solution is introduced through the cannula or tubing inserted into the central lumen 17 of chamber 8 of the balloon catheter and flows out of the balloon catheter chamber 8 to the surrounding tissues from the distal opening 18 of the balloon catheter 2. A cannula of a length equal to the length of chamber 8 of the balloon catheter, is a preferred delivery system. The cannula is preferably connected to a syringe pump filled with the washing solution. Pressure is preferred as a delivery means so that manual application and subsequent retrieval of the washing solution by gentle suction can be easily done several times. Application pressure is applied by pushing the barrel of the syringe forward. Retrieval of the washing solution is done through suction by pulling the barrel backwards to create a negative pressure thereby directing the flow back to the syringe barrel. For the glaucoma filtration procedure, a volume of at least 30 ml. is sufficient to wash off the wound modulating agent such as mitomycin. After the washing procedure, a fistula through the sclera on the limbus portion of the eye and into the anterior chamber can be formed through means known in the art.

Figure 9:
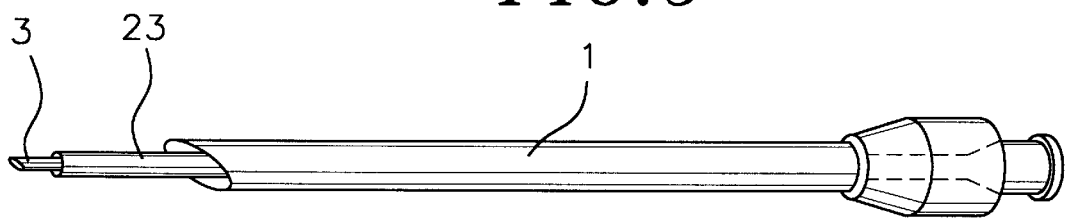
FIG. 9 illustrates a needle inside a cannula inserted through a catheter sheath.

A further specific application of the catheter system of the invention is for scar revision to repair previous glaucoma filtration procedures which have failed. As indicated above, glaucoma filtration procedures usually fail when collagenous scars subsequently forms on the fistula and the surrounding tissue, sometime after the filtration procedure, thereby blocking the flow of the aqueous humor. Scar revision as used in this invention means creating channels through the scars formed after an unsuccessful filtration procedure so that the aqueous humor can again flow from the anterior chamber of the eye thereby preventing the build up of the intraocular pressure (TOP) of the eye. The method for the scar revision follows basically the same steps as the glaucoma filtration procedure up to the introduction and washing of the wound modulating agent. An initial incision on the subconjunctiva is made with a needle 3 covered by a catheter sheath 1 as shown in FIG. 2. The needle inside the catheter sheath is retrieved and the sheath is advanced to the desired tissue location. As in the glaucoma filtration procedure described above, the catheter sheath may be tapered to allow anchoring of the sheath into the incision or if a straight tubular catheter sheath is used, the catheter sheath may be anchored in place by a sleeve 5 through tamponing as shown in FIG. 4A or by advancing the sleeve downward through the sheath in contact with the tissue until the tissue 21 rests on the recessed portion 6 of the sleeve as shown in FIG. 4B. A balloon catheter 2 is introduced through the lumen 7 of the catheter sheath 1 and advanced to the location of the scar. The scarred region may not be confined in one area. The rigid tip portion 10 at the distal end of the balloon catheter 2 enables the balloon catheter to enter into the scar formations. The desired substance, a wound modulating agent such as mitomycin is delivered to the scarred area through the expandable portion 13 of the balloon catheter 2. The expandable portion of the balloon catheter 2 should protrude beyond the distal tip of the catheter sheath 1, preferably by 0.5 inch as shown in FIG. 1 to allow the flow of the antimetabolite to the scarred regions. Immediately after the application of the wound modulating agent, the balloon catheter 2 is deflated and the agent withdrawn from chamber 9. Washing solution is then applied through a cannula connected to a syringe pump or tubing introduced through lumen 17 of chamber 8 of the balloon as shown in FIG. 6. The washing solution is repeatedly applied to the scar formations by flushing followed by gentle suction to remove the antimetabolite from the scarred regions. At least 100 milliters of washing solution is applied to each treated scar formation. After washing, the balloon catheter is retrieved from the catheter sheath 1 and replaced with a needle 3. The needle is used to create more channels through the scars aside from the one created by the introduction of the balloon catheter 2. Channels are created by poking the needle at several locations of the scar formations. For scar revision, a 27 gauge needle, 1.25 inch in length is preferred. It is most preferred to introduce the needle 3 through a 20 gauge metal cannula 23 prior to introduction into the catheter sheath 1 as shown in FIG. 9 to prevent the needle from penetrating through the catheter sheath which avoids accidental poking of the tissues around the scar. The needle is preferably connected to a syringe by a luer lock connection. The barrel of the syringe which is of a diameter larger than the cannula, limits further advancement of the needle into the scar formation to prevent poking of tissues underneath the scar formation. At full insertion of the needle ended syringe inside the cannula 23, the tip of the needle preferably protrudes 1 mm from the tip of the metal cannula 23. The wound modulating agent, such as mitomycin, when applied to the scarred regions well prevent reformation of the scar on the channels formed after the application and washing of the wound modulating agent. More permanent openings are created through which the aqueous humor may flow through to prevent increase of IOP.

FIGS. 1–9 illustrate the preferred and various alternate designs of the catheter system in accordance with the invention. The catheter system as shown in FIG. 1 comprises of a catheter sheath 1 through which other devices may be inserted other than a balloon catheter, and the balloon catheter 2 for administering a desired substance or substances into a localized area of an internal tissue or organ. The catheter sheath 1 has an elongated nonexpendable tubular shaft with a distal and a proximal end and an opening therethrough forming a lumen 7 as shown in FIGS. 3A and 3B. The proximal end of catheter sheath 1 preferably terminates with an enlarged opening 4 for easy introduction of other known devices. An example of such device is a needle 3 with a luer lock at one end opposite the sharp end as shown in FIG. 2 which can be introduced through the catheter sheath 1 until further entry of the needle is restrained when the luer lock tip comes in contact with the walls of the enlarged opening 4 of the catheter sheath. FIG. 2 illustrates the insertion of needle 3 into the lumen 7 of the catheter sheath 1. The tapered catheter sheath with the enlarged opening at the proximal end as shown in FIG. 3B allows for both easy introduction of other devices and anchoring of the catheter sheath into the incision. The length of the catheter sheath is dependent upon the distance from the site of incision to the tissue or organ to which the drug or substance is to be applied. The tubular portion of the catheter sheath 1 is usually formed from biocompatible medical grade polymeric material by conventional techniques such as extrusion or fabrication from appropriate sheet stock. A biocompatible medical grade polymeric material means a material that is nonreactive to bodily tissues and fluids for a relatively long periods of time. The catheter sheath is preferably 14–16 gauge. A sleeve 5 may be used to anchor the catheter sheath into the surrounding tissue or organ as shown in FIGS. 4A and 4B. The sleeve 5 is either trapezoidal or dumbbell shaped with a tubular bore at the center running horizontally from end to end as shown in FIGS. 5A and 5B. The dumbbell shaped sleeve as shown in FIG. 5B has a recessed portion 6. The length of the sleeve is dependent upon the length of the catheter sheath 1 and the type of tissue or organ to which the catheter sheath 1 is to anchor on. The bore diameter of the sleeve 5 is slightly larger than the outer diameter of the catheter sheath 1. When the sleeve is used for anchoring, the sleeve 5 is pushed back to the proximal end of the catheter sheath 1 before use. The bore running through the center of the sleeve is preferably tapered with the bore diameter at the proximal end slightly smaller than the bore diameter at the distal end of the sleeve as shown in FIG. 4. The proximal end of the sleeve snug fits on the proximal end of the catheter sheath to prevent the sleeve from sliding down the catheter sheath on its own prior to use. The bore diameter of the sleeve has an outer diameter 0.5 mm to 1 mm larger than the diameter of the catheter sheath. The sleeve is made of a biomedical grade polymeric material. The sleeve 5 may be rigid or flexible. The balloon catheter 2 consists of a nonexpendable tubular core having separate chambers a first chamber 8 and a second chamber 9 to allow separate and independent introduction of different substances from the same balloon catheter. The separate chambers allow simultaneous or sequential delivery of the different substances into the desired location. Additional chambers, if required by the intended procedure, may be constructed similarly as chamber 8 within the balloon catheter and is still within the contemplated scope of the invention. The diameter of the catheter system described is increased as more chambers within the balloon catheter is added. The thickness of the walls of the chambers may be varied depending upon the desired rigidness, the tolerated diameter and length for tissue insertion, and the pressure to be exerted and withstood within the inside compartment of the chambers within the balloon catheter. The nonexpendable portion of the balloon catheter is made of biocompatible medical grade polymeric material. The balloon catheter 2 is preferably cylindrical extending horizontally from a distal to a proximal end. At the distal end of the catheter 2 is a tip portion 10 which is relatively rigid and capable of dissecting bodily tissues. Chamber 8 is a hallow chamber cylindrical in shape extending horizontally through the length of the balloon catheter 2. The distal end of chamber 8 is in direct communication with the tip 10. At the distal end of chamber 8 near the tip 10 is at least one opening 18 to allow the flow of substances out of the balloon catheter from chamber 8. At the proximal end of chamber 8 is an enlarged opening 11, preferably conical or funnel shaped for easy introduction of other devices into the lumen 17 of the chamber. As shown in FIGS. 6 and 7, lumen 17 directly communicates the distal opening 18 with the proximal opening 11 to allow free flow of substances from chamber 8. The first chamber 8 has an inner wall 26 lining lumen 17 and an outer wall 27 which is also the inner wall of the second chamber 9. Surrounding chamber 8 is a separate chamber 9 which is preferably constructed concentrically around chamber 8. Chamber 9 is also a hollow chamber cylindrical in shape extending through the length of chamber 8. The outer wall 19 of chamber 9 borders the outer diameter of the balloon catheter 2 while the inner wall 27 is the same as the outer wall of the first chamber 8 and borders the outer diameter 20 of chamber 8. Chamber 9 provide another means for introducing other desired substances independent of chamber 8. At the proximate end of chamber 9 is an opening 15 through which a desired substance can be introduced through the lumen 16. The opening 15 is preferably on the side away from the opening 11 of chamber 8 as shown in FIG. 7 and 8. The distal end of chamber 9 is closed. At the outer wall 19 bordering the outer diameter of chamber 9 near its distal end are openings 12 through which the substances introduced through the lumen 16 of chamber 9 can flow through. Covering the openings 12 and some portion of the nonexpendable outer wall of chamber 9, is an expandable membrane 13 made up of a semi-permeable or microporous membrane. For the glaucoma filtration procedure, the preferred portion covered by the expandable membrane is approximately 4 mm. in length. As used herein, expandable includes the connotation that the expanding element will return to its unexpanded configuration upon removal of the force causing the expansion. The length of the balloon catheter 2 is such that the expandable membrane portion 13 of the balloon catheter will protrude beyond the distal tip of catheter sheath 1 when the balloon catheter is introduced through lumen 7 of the catheter sheath 1 as shown in FIG. 1.

The porosity of the semipermeable or microporous membrane should be such that diffusion of the desired substance from the membrane surface can be controlled. The semipermeable or microporous membrane may be molded to, adhesively adhered or bonded over the openings 12 on the outer wall 19 of the nonexpendable core of the balloon catheter 2 defining chamber 9. When positive pressure is applied to chamber 9 through its lumen 16, the membrane adhesively adhered to the nonexpendable core of the balloon catheter inflates or expands to form a balloon chamber 14. The applied pressure is transported to the expandable membrane through the openings 12 on the outer wall 19 of chamber 9. Examples of materials from which semipermeable and microporous membranes can be constructed are cellulose acetate, polyacrylonitrile, cellulose, polyvinyl chloride, polysulfone, silicon, polyurethanes, natural and synthetic elastomers, polyesters, and polyolefins. Semipermeable and microporous membranes usually have pore sizes smaller than one micron. The preferred pore size and the part cedar material of the expandable portion of the balloon catheter will depend upon the molecular size, chemical composition, and molecular shape of the substance to be transported across the membrane as well as the transport means used. Semipermeable or microporous membranes are preferred because blood and other body secretions will not cross the membrane and enter chamber 9 during the deflation of the balloon after the introduction of the desired substance or when the nonpressure force that transported the substance is terminated. The semipermeable and microporous membranes that satisfy the requirement of the invention can be manufactured in any several ways, most of which are readily understood by those skilled in the art of manufacturing microfiltration and ultrafiltration membranes.

In addition to the use of the catheter system in the management of glaucoma, the usefulness of the present apparatus arid method for he other surgical procedures and treatment of other diseases will be appreciated by those skilled in the art.

What is claimed is:

1. A method for correcting glaucoma comprising:
   (a) introducing a catheter sheath having a holding means to a desired location of the eye;
   (b) inserting a balloon catheter having a first and second chamber into the catheter sheath;
   (c) delivering a wound modulating agent through the second chamber of the balloon catheter to the desired location of the eye;
   (d) washing the applied wound modulating agent with a washing solution introduced into the first chamber of the balloon catheter; and
   (e) creating a fistula through the desired location of the eye.

2. The method of claim 1 wherein the fistula of step (d) is formed through the sclera near the limbus portion of the eye and into the anterior chamber.

3. The method of claim 1 wherein the wound modulating agent is selected from the group consisting of alkylating drugs, antimetabolites and natural alkaloids.

4. The method of claim 3 wherein the wound modulating agent is Mitomycin-C.

5. The method of claim 4 wherein the concentration of Mitomycin-C is 0.001%–0.06%.

6. The method of claim 1 wherein the catheter sheath is introduced into the episcleral space of the eye.

7. The method of claim 1 further comprising, after step (a), anchoring the catheter sheath having a holding means to keep the catheter in place.

8. A method for repairing a failed glaucoma filtration procedure by scar revision, comprising:
   (a) introducing a catheter sheath having a holding means to a desired location;
   (b) inserting a balloon catheter having a rigid tip portion and a first and second chamber into the catheter sheath;
   (c) delivering a wound modulating agent through the second chamber of the balloon catheter to a scar formation;
   (d) washing the applied wound modulating agent with a washing solution introduced into the first chamber of the balloon catheter; and
   (e) poking a rigid tipped object through the scar formation to create channels through the scar formation.

9. The method of claim 8 further comprising after step (c), introducing a cannula into the first chamber of the balloon catheter.

10. The method of claim 8 wherein the rigid tipped object of step (e) is introduced inside the catheter sheath prior to poking the scar formations.

11. The method of claim 10 wherein the rigid tipped object is introduced into a cannula to cover the rigid tipped object prior to introducing the rigid tipped object into the catheter sheath.

12. The method of claim 8 further comprising, after step (a), anchoring the catheter sheath having a holding means to keep the catheter in place.

* * * * *